United States Patent [19]

Hider et al.

[11] Patent Number: 4,866,052
[45] Date of Patent: Sep. 12, 1989

[54] TREATMENT OF SICKLE CELL DISEASE

[75] Inventors: Robert C. Hider, Clacton; Ernst R. Huehns, London, both of England

[73] Assignee: National Research Development Corporation, London, England

[21] Appl. No.: 124,115

[22] PCT Filed: Mar. 19, 1987

[86] PCT No.: PCT/GB87/00194

§ 371 Date: Nov. 2, 1987

§ 102(e) Date: Nov. 2, 1987

[87] PCT Pub. No.: WO87/05509

PCT Pub. Date: Sep. 24, 1987

[30] Foreign Application Priority Data

Mar. 20, 1986 [GB] United Kingdom ................. 8606913

[51] Int. Cl.$^4$ .......................................... A61K 31/555
[52] U.S. Cl. ..................................... 514/184; 514/188
[58] Field of Search ................................ 514/184, 188

[56] References Cited

U.S. PATENT DOCUMENTS 4,665,064  5/1987  Hider et al. .......................... 514/184

FOREIGN PATENT DOCUMENTS 0022229  1/1981  European Pat. Off. .
0145228  6/1985  European Pat. Off. .
2148896  6/1985  United Kingdom .

OTHER PUBLICATIONS

Gilman, J. G. et al, "The Oxygen-Linked Zinc-Binding . . .", Biochem. J. (1978) 169, pp. 625–632.
Brewer, G. J. et al, "Suppression of Irreversibly Sickled . . .", J. lab. Chem. Med., Sep. 1977, pp. 549–554.
Arnone, A. et al, "The Binding of Zinc to Human . . .",
Zinc Metabolism: Current Aspects in Health & Disease, 1977, pp. 317–328.
Weatherall, D. J. et al, "Haemolytic Anemia . . .", Oxford Textbook of Med., vol. 2, Sec. 13–Index 1983, pp. 19.62–19.66.
Brewer G. J., "Interactions of Trace Elements . . .", Jour. of Ame. College of Nutrition 4:33–38 (1985).
Oelshlegel, Jr. G. J. et al, "Studies on the Interaction of . . .", Archives of Biochem. & Biophysics, 163, 742–748 (1974).
Brewer, G. J. et al, "Suppression of Irreversibly Erythrocytes by . . .", J. Lab. Clin. Med., vol. 90, No. 3, Sep. 1977, pp. 549–554.
Oelshlegel, F. J., "Effect of Zinc on Increasing Oxygen . . .", Biochemical & Biophysical Res. Communications, vol. 53, No. 2, 17 Jul. 1973, Academic Press, Inc. pp. 560–566.
Schoomaker, E. B. et al, "Zinc in the Treatment of Homozygous. . . . ", American Jour. of Hematology, vol. 1, No. 1, 1976, pp. 45–57.
Brewer, G. J., "Detours of the Road to Successful . . .", Perspect Biol. Med., vol. 22, No. 2, Part 1, Winter 1979, pp. 250–272.

Primary Examiner—Curtis R. Davis
Attorney, Agent, or Firm—Nixon & Vanderhye

[57] ABSTRACT

Neutral 2:1 ligand:zinc(II) complexes in which at least one ligand is provided by a compound being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms are of value for use in effecting an enhancement of the oxygen binding ability of a patient's haemoglobin, this being of particular application in the treatment of sickle cell disease.

22 Claims, 2 Drawing Sheets

TREATMENT OF SICKLE CELL DISEASE

This invention relates to the treatment of sickle cell disease and other conditions benefiting from the modification of haemoglobin to enhance its oxygen carrying characteristics.

Sickle cell disease comprises a group of disorders resulting from a hereditary defect which causes a modification of the normal AA haemoglobin to haemoglobin of the SS, SC, SD or Sβthal form and leads to a polymerisation of the haemoglobin when in the deoxy state to form a linear polymer of a sickle shape. The sickle cells are less readily able to pass through the capilliaries resulting in repeated painful crises for the patient.

Various treatments have been developed for sickle cell disease involving the oral administration to the patient of one of several drugs having an influence on the behaviour of the haemoglobin molecules, these drugs including cyanates, urea and zinc salts Although each of the drugs can have some beneficial effect, none of them is really satisfactory and there is still a need for an effective treatment for alleviation of the recurrent pain crises in sickle cell disease.

In UK Patent Application No. 8427485 (published as GB 2148896A) and in equivalent applications (European Patent Application No. 84307511.0, Japanese Patent Appliction No. 84/231136, U.S. Pat. No. 666905, now U.S. Pat. No. 4,665,064, etc.) a wide range of zinc complexes is described for administration to patients to treat zinc depletion but no mention is made therein of the donation of zinc from the complexes to haemoglobin and, indeed, it is indicated therein that when administered to a patient the zinc becomes predominantly bound to apotransferrin. We have now found that certain of this group of zinc complexes may be used with advantage for alleviating the effects of sickle cell disease in a treatment involving an extra-corporeal processing of the patient's blood.

Accordingly the present invention comprises the use of a neutral 2:1 ligand:zinc(II) complex in which at least one ligand is provided by a compound being 3-hydroxy-4-pyrone or a 3-hydroxy-pyrone in which one or more of the hydrogen atoms attached to ring carbon atoms are replaced by an aliphatic hydrocarbon group of 1 to 6 carbon atoms, for the manufacture of a medicament for use in the treatment of sickle cell disease.

The zinc complexes of the present invention are of particular interest in that they include several compounds which have previously been used either as the metal-free compound or as its iron complex in foodstuffs, thereby indicating their non-toxic nature and the consequent suitability for pharmaceutical use of the zinc complexes of these compounds.

The 2:1 zinc complexes used in the present invention contain zinc in the divalent state and are neutral, there being an internal balance of charges between the metal cation and the two monobasic, bidentate ligands bound covalently thereto. The hydroxypyrones described above will provide such a monobasic, bidentate ligand by the loss of a proton from the hydroxy group (OH→O⁻). Although the complexes used in the present invention are required to contain at least one hydroxypyrone ligand, the second ligand may if desired be derived from any alternative compound which will provide a physiologically acceptable, monobasic, bidentate ligand which is capable of binding to zinc. The inclusion in a complex of two different ligands can produce an added dimension to the design of complexes having optimised properties for uptake by erythrocytes. However, both ligands are more conveniently derived from a hydroxypyrone and, in general, complexes containing two identical hydroxypyrone ligands are preferred by virtue of their greater simplicity of preparation and use.

It will be appreciated that the zinc complexes used in the present invention may exist in either a tetrahedral or an octahedral form since, although complexes containing a 2:1 proportion of monobasic, bidentate ligand:zinc(II) will usually have the tetrahedral form, it is possible for them to adopt the octahedral form by combination with two additional neutral ligands, in particular water molecules. The neutral 2:1 complexes may conveniently therefore be used in either the anhydrous or the dihydrate form, the anhydrous form possibly being converted to the dihydrate form in an in vivo aqueous environment.

As regards the hydroxypyrone ligands, the substituted 3-hydroxy-4-pyrones may carry more than one type of aliphatic hydrocarbon group but this is not usual and, indeed, substitution by one rather than two or three aliphatic hydrocarbon groups is preferred. The term aliphatic hydrocarbon group is used herein to include both acyclic and cyclic groups which may be unsaturated or saturated, the acyclic groups having a branched chain or especially a straight chain. Groups of 1 to 4 carbon atoms and particularly of 1 to 3 carbon atoms are of most interest. Saturated aliphatic hydrocarbon groups are preferred, these being either cyclic groups such as the cycloalkyl groups cyclopropyl and especially cyclohexyl or, more particularly, acyclic groups such as the alkyl groups methyl and particularly n-propyl and isopropyl, and especially ethyl. Substitution at the 2- or 6-position is of especial interest although, when the ring is substituted by the larger aliphatic hydrocarbon groups, there may be an advantage in avoiding substitution on a carbon atom alpha to the

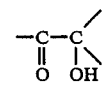

system.

This system is involved in the complexing with zinc and the close proximity of one of the larger aliphatic hydrocarbon groups, for example one of more than 4 carbon atoms, may lead to steric effects which inhibit complex formation.

Examples of hydroxypyrones providing ligands which may be used in complexes according to the present invention have the formula (I), specific hydroxypyrones of particular interest having the formulae (II) and (III):

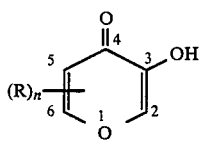 (I)

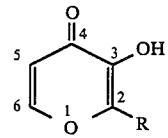 (II)

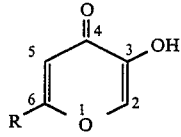 (III)

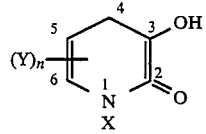 (IV)

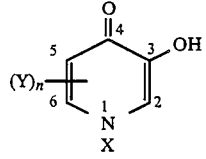 (V)

in which R is an alkyl or cycloalkyl group, for example methyl, ethyl, n-propyl, isopropyl or butyl, and n is 0, 1, 2 or 3 (the ring being unsubstituted by any alkyl group when n is 0). Among these compounds 3-hydroxy-2-methyl-4-pyrone (maltol; II, R=CH$_3$), 3-hydroxy-2-propyl-4-pyrone (II, R=CH$_2$CH$_2$CH$_3$), 3-hydroxy-2-(2'-methylethyl)-4-pyrone (II, R =CH(CH$_3$)$_2$) and especially 2-ethyl-3-hydroxy-4-pyrone (II, R=C$_2$H$_5$) are of most interest, although 3-hydroxy-4-pyrone (I, n =0) and 3-hydroxy-6-methyl-4-pyrone (III, R=CH$_3$) are also of especial interest.

As regards the non-hydroxypyrone ligands, these may be derived from various forms of compound and include those physiologically acceptable, monobasic, bidentate ligands capable of binding to zinc which are known in the art. The compounds which provide such ligands will generally comprise (a) a first grouping containing an acidic proton which is lost to provide both the single negative charge on the ligand and also one of its chelating sites and (b) a second grouping which provides the second chelating site. One group of compounds of particular interest is the 3-hydroxypyrid-2- and -4-ones in which the grouping (a) is an enolic hydroxy group and the grouping (b) is an oxo group. Preferred compounds of this group are a 3-hydroxypyrid-2-one or 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, cycloalkoxy, aliphatic amide, aliphatic ester, halogen and hydroxy groups and, optionally, in which one or more of the hydrogen atoms attached to ring carbon atoms are replaced by one of said substituents, by an aliphatic hydrocarbon group of 1 to 6 carbon atoms, or by an aliphatic hydrocarbon group substituted by an alkoxy, cycloalkoxy, aliphatic ester, halogen or hydroxy group. Such hydroxypyridones have the formulae (IV) and (V)

in which X and Y are substituents as defined hereinbefore in relation to possible C- and N-substituents on 3-hydroxypyridones and n is 0, 1, 2 or 3.

The 3-hydroxypyrid-2-ones are generally of somewhat greater interest than the 3-hydroxypyrid-4-ones, due to the larger partition coefficients of zinc complexes containing ligands provided by compounds of the former group. Other detailed preferences relating to the nature and position of the substituent groups present in the hydroxypyridones.-. are broadly as expressed in relation to hydroxypyridone iron complexes in UK Patent No. 2117766 and in equivalent Applications (European Patent Application No. 83301660.3, Japanese Patent Application No. 83/049677, U.S. patent application No. 478494, etc.) and in UK Patent Application No. 8407180, published as GB 2136806A, and in equivalent Applications (European Patent Application No. 84301882, Japanese Patent Application No. 84/057186, U.S. Pat. No. 592543, now U.S. Pat. No. 4,650,793, etc.). Thus substituted aliphatic hydrocarbon groups present in the hydroxypyridones may as indicated therein carry more than one substituent group, but it is preferred that only one substituent group is present. Such substituted aliphatic hydrocarbon group substituents may conveniently derive from aliphatic hydrocarbon groups of 1 to 8 and particularly of 1 to 6 carbon atoms. However, the simpler hydroxypyridones of UK Patent Application GB 2118176A containing only unsubstituted aliphatic hydrocarbon group substituents of 1 to 6 carbon atoms are of the greatest interest. The preferences among the aliphatic hydrocarbon groups present in these hydroxypyridones correspond largely to those expressed in relation to the hydroxypyrones, with methyl groups conveniently being used for substitution on ring carbon atoms but larger alkyl or cycloalkyl groups also being of particular interest for substitution on the ring nitrogen atoms. Substitution of the ring carbon atoms, which is again preferably by one rather than two or three aliphatic hydrocarbon groups, is of particular interest in the case of the 3-hydroxypyrid-4-ones, for example at the 6- or particularly the 2-position, whilst the 3-hydroxypyrid-2-ones may more often be used without any additional aliphatic hydrocarbon group substituent on the ring carbon atoms. Specific hydroxypyridones of particular interest have formulae (VI), (VII), (VII), and (VIII)

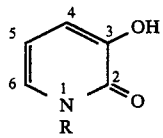 (VI)

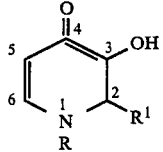 (VII)

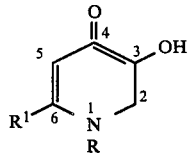 (VIII)

in which R is an alkyl group, for example methyl, ethyl, n-propyl, isopropyl or butyl, and $R^1$ is hydrogen or particularly an alkyl group, for example methyl. Among such compounds 1-ethyl-3-hydroxy pyrid-2-one, 3-hydroxy-1-propylpyrid-2-one, 3-hydroxy-1-(2metyyl-ethyl)-pyrid-2-one, 1-butyl-3-hydroxypyrid-2-one, 1-ethyl-2-methyl-3-hydroxypyrid-4-one, 2-methyl-1-propyl-3-hydroxypyrid-4-one, 3-hydroxy-2-methyl-1-(2'-methylethyl)-pyrid-4-one and 1-butyl-hydroxy-2-methylpyrid-4-one are of particular interest with the 3-hydroxypyrid-2-ones such as 1-ethyl-3-hydroxypyrid-2-one being especially preferred.

Other non-hydroxypyrone ligands of especial interest may be derived from compounds containing groupings (a) and (b) as described above where the grouping (a) is either an enolic hydroxy group or a carboxy group whilst the grouping (b) is an amine group, conveniently a primary amino group, or a hydroxy group. In a particular case, one grouping can fulfil both function (a) and function (b). Thus, some aliphatic monocarboxylic acids can provide an anion capable of a bidentate mode containing a grouping

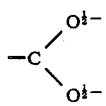

which will fulfill both functions.

Apart from such aliphatic monocarboxylic acids, particularly those alkanoic acids containing from 1 to 5 carbon atoms such as formic acid, propionic acid and particularly acetic acid, many other forms of acid are of interest for providing alternative non-hydroxypyrone ligands. These include various hydroxy acids, for example lactic acid, gluconic acid, etc., and various amino acids, for example glycine, isoleucine, leucine, methionine, phenylalanine, tyrosine and valine. Also of interest are peptides, particularly the smaller compounds such as tri- and especially di-peptides, for example those containing the same or different amino acids selected from those listed above such as glycyl-leucine, leucyl-glycine and especially glycyl-glycine and leucyl-leucine. Apart from such carboxylic acids, the other group of compounds of particular interest is those containing a grouping

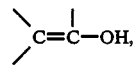

a particular example of this class being ascorbic acid (vitamin C). It should be noted that ascorbic acid is capable of providing a dibasic rather than a monobasic anion but compounds such as this are quite suitable for use in providing ligands of use in the zinc complexes where they have a single pKa, only, which is less than 10, since in use under physiological conditions the ascorbate or other such anion will be monobasic. It will be appreciated from the foregoing discussion that the carbohydrate compounds gluconic acid and ascorbic acid are of interest in providing ligands and this interest extends to other carbohydrates, including particularly the monosaccharide sugars and related compounds. In selecting carbohydrate or other compounds for providing ligands, the more hydrophobic compounds are generally of greater interest so that among the amino acids, for example, the more complex amino acids than glycine may be of greater value.

Among the quite wide range of ligands described above certain ligands or combinations of ligands will be of particular value and some indication of these has already been given. One measure of the value of the different complexes is provided by the value of their partition coefficient ($K_{part}$) between n-octanol and Tris hydrochloride (20 mM, pH 7.4; Tris representing 2-amino-2 hydroxymethylpropane 1,3-diol) at 20° C., this being expressed as the ratio (concentration in organic phase)/(concentration in aqueous phase). Preferred complexes show a value of $K_{part}$ for each ligand-providing compound of above 0.02 or 0.05 but less than 3.0, especially of above 0.2 but less than 1.0, together with a value of $K_{part}$ for the 2:1 zinc(II) complex of above 0.02 but less than 6.0, especially of 0.05 or 0.1 to 1.0.

Examples of specific zinc(II) complexes of use in the present invention are those complexes containing two identical ligands drawn from the hydroxypyrones named hereinbefore as being of particular interest, especially zinc(II) (3-hydroxy-2-methyl--pyrone)2, zinc(II) (3-hydroxy-2-(2'-methylethyl)-4-pyrone)2, zinc(II) (3-hydroxy-2-propyl-4-pyrone)2 and zinc(II) (2-ethyl-hydroxy-4-pyrone)2, these complexes having partition coefficients of 0.1, 2.2, about 2 and 1.2, respectively. Among complexes containing two different ligands, specific examples are zinc(II) (2-ethyl-3-hydroxy-4-pyrone) (1-ethyl-3-hydroxypyrid-2-one), zinc(II) (2-ethyl-3-hydroxy-4-pyrone) (leucine), zinc(II) (2-ethyl-3-hydroxy-4-pyrone) (glycine), zinc(II) (2-ethyl-3-hydroxy-4-pyrone) (ascorbic acid), zinc(II) (2-ethyl-3-hydroxy-4-pyrone) (gluconic acid) and especially complexes containing each of the possible combinations of mixed ligands selected from the group consisting of 3-hydroxy-2-methyl-4-pyrone, 3-hydroxy-2-(2'-methylethyl)-4-pyrone, 3-hydroxy-2-propyl-4-pyrone and 2-ethyl-3-hydroxy-4-pyrone, particularly those containing the last mentioned ligand as one of the two present in the complex, such as zinc (II) (2-ethyl-3-hydroxy-4-pyrone) (3-hydroxy-2-methyl-4-pyrone). It will be appreciated that the names of the hydroxypyrones are used in the names of these complexes to represent the ligands derived therefrom, and similarly for the other ligands, this usage being employed throughout the specification.

Where desired, a mixture of two or more zinc complexes may be used in the present invention, for example a mixture of any two of the hydroxypyrone complexes containing identical ligands which are specifically named above.

The zinc complexes are conveniently prepared in the solid state by the reaction in a suitable mutual solvent of the ligand-providing compound(s) and zinc ions, the latter conveniently being derived from a zinc salt, particularly a zinc halide and especially zinc chloride. For the best results, it is preferred to avoid the use of water alone as a reaction solvent, the use of an aqueous/organic solvent mixture or particularly an organic solvent being preferred. The solvent may, for example, be ethanol, methanol or chloroform and mixtures of these solvents together and/or with water where appropriate. In particular, methanol or especially ethanol, or a mixture thereof with chloroform, may be used where it is desired to effect the separation of at least a major part of a by-product such as sodium chloride by precipitation whilst the zinc complex is retained in solution.

The nature of the product obtained will depend not only upon the molar proportion of the various reactants but also upon the pH of the reaction medium. Thus, for the preparation of the neutral 2:1 zinc complexes the ligand-providing compound(s) and the zinc salt are conveniently mixed in solution in a 2:1 molar proportion and the pH adjusted to a value in the range of 6 to 9, for example 7 or 8. If a similar excess of the compound(s):zinc is employed but no adjustment is made of the acidic pH which results on the admixture of the compound(s) and a zinc salt such as zinc chloride then a mixture of the 2:1 complex or complexes and the 1:1 complex or complexes will be obtained. However, when as discussed hereinafter it is desired to use the 2:1 zinc complex together with an excess of the metal-free ligand-providing compound(s), this may be achieved by using a greater molar proportion of the compound(s):zinc than 2:1 in the reaction mixture to thereby provide a product containing such an excess.

Adjustment of the pH may conveniently be effected by the addition either of sodium carbonate or of a hydroxide base such as sodium or ammonium hydroxide, the use of a hydroxide base being of particular interest when preparing the zinc complexes in batches of 20 g or more. When using a hydroxide base, the reaction may conveniently be carried out in a medium containing a proportion of water as the solvent, for example in an ethanol:water mixture such as 4:1 v/v ethanol:water, and the pH adjusted by the addition of a 2 molar aqueous solution of the base. It will be appreciated that the presence of water in the reaction mixture will lead to the retention of a by-product in the zinc complex on evaporation of the solvent (a chloride where the zinc salt is zinc chloride). However, this can be removed, if desired, by procedures such as crystallisation from a suitable solvent system where possible or sublimation in the particular case of amnonium chloride. In general, however, the use of a non-aqueous reaction medium in conjunction with sodium carbonate is preferred.

When preparing a 2:1 zinc(II) complex containing different ligands, the individual ligand-providing compounds may conveniently each be used in a 1 molar proportion, together with a 1 molar proportion of the zinc salt. It will be appreciated, however, that the use of such a proportion will not lead exclusively to the mixed 2:1 ligand:zinc(II) complex since, although this form of complex will predominate providing the ligand-providing compounds are of similar reactivity, it will be obtained in admixture with the two 2:1 complexes containing identical ligands.

Reaction to form the zinc complex is generally rapid and will usually have proceeded substantially to completion after 5 minutes at about 20° C., although a longer reaction time may be used if necessary. Following separation of any precipitated by-product, such as a sodium chloride in the case of certain solvent systems, the reaction mixture may conveniently be evaporated on a rotary evaporator or freeze dried to yield the zinc complex which is usually in solid form. A solid complex may, if desired, be crystallised from a suitable solvent, for example water, an alcohol such as ethanol, or a solvent mixture, including mixtures containing an ether. Whether the zinc complex is obtained in anhydrous or dihydrate form will depend both on the solvent system used for the reaction and on the subsequent working up procedure. Thus rigorous drying may remove the water molecules from a hydrated complex formed in a reaction mixture containing water and recrystallisation from an aqueous medium may add them. If a dihydrate is specifically required, freeze drying of the mixture resulting from the reaction of the ligand-providing compound(s) and zinc salt such as the chloride or acetate in an aqueous/organic solvent medium may be employed.

As an alternative to the above procedures directed to the preparation of complexes in the solid state, aqueous solutions of zinc hydroxypyrone complexes, for example, may conveniently also be prepared directly by dissolving a zinc salt, for example zinc sulphate, and the hydroxypyrone in water and adjusting the pH of the solution to between 7.0 and 8.0, for example 7.4. Thus, the (addition of zinc sulphate (25 mmoles) to a solution of 2-ethyl-3-hydroxy-4-pyrone ($25 \times 10^2$ mM) in water (100 ml) leads to the complete chelation of the zinc when the pH is adjusted to 7.4 by the addition of a base, for example sodium hydroxide.

The preparation of the complexes is exemplified in UK Patent Application No. 8427485 and its equivalents.

Certain of the ligand-providing compounds, such as 3-hydroxy-2-methyl-4-pyrone, are available commercially. With other hydroxypyrones a convenient starting material in many instances consists of pyromeconic acid which is readily obtainable by the decarboxylation of meconic acid and may be reacted with an aldehyde to insert a 1-hydroxyalkyl group at the 2-position, which group may then be reduced to produce a 2-alkyl-3-hydroxy-4-pyrone. The preparation of 2-ethyl-3-hydroxy-4-pyrone, etc., by this route is described in the published U.S. application Ser. No. 310,141 (series of 1960).

Treatment of the patient's blood with the zinc complex medicaments according to the present invention will usually involve removal of an aliquot of the patient's blood, conveniently by venipuncture, treatment of the blood with the complex, preferably under conditions of time and relative concentration o erythrocytes and zinc complex which, without producing any undesirable side effects, are such as to maximise the enhancement of the oxygen binding ability of the patient's haemoglobin (a maximum level of binding involving substantial saturation of the two main zinc binding sites in each haemoglobin molecule), and return of the blood to the patient. The procedure may then be repeated, conveniently using between two and six cycles, for example four cycles, for each treatment session, a convenient volume of blood to be treated as an aliquot consisting of between 200 and 500 ml, for example 350 ml, for adults with proportionately smaller volumes for children. The appropriate period for the processing of each aliquot and to some extent the concentration of the zinc complex relative to the erythrocytes will depend in part upon the particular complex used. However, a suitable period is often in the region of 15 to 45 minutes, for example 20 and especially 30 minutes.

Although it has been found that an increase in concentration of the zinc complex used in the treatment of the patient's blood leads to an increase in the level of binding of zinc to the haemoglobin and consequently in the enhancement of the oxygen binding ability thereof, it has also been found that the use of the complex at too high a concentration level can have an effect on the erythrocytes which lowers their half life. This leads to the surprising result that the optimum concentrations of the zinc complex are quite low, the increased ability of the zinc complexes to produce a left shift of the oxygen dissociation curve, as described hereinafter, in the case of sickle erythrocytes as compared with normal erythrocytes being one factor which makes possible the use of such low concentrations. The preferred concentrations of the complex are most conveniently expressed in terms of the molar concentration of zinc (as the zinc complex) in the blood treatment medium in order to take account of the varying proportion by weight of zinc in complexes containing ligands of varying molecular weight, although even so the preferred range may depend somewhat upon the particular complex being used. As a guide, however, it may be stated that, although levels of as high as about $10^{-2}$ molar (10 mM) may be used with marked beneficial effect on the oxygen binding ability of the patient's haemoglobin, these levels will shorten the half life of the erythrocytes. Preferably, therefore, lower levels are used which have little or no such effect whilst retaining a measure of enhancement of oxygen binding ability, for example a concentration of zinc (as the zinc complex) of $10^{-3}$ to $10^{-5}$ molar. However, some slight reduction of half life has still been observed at a zinc concentration of $10^{-3}$ molar and a value less than this is therefore preferred, a convenient range for the concentration of zinc (as the zinc complex) being $5 \times 10^{-4}$ to $10^{-5}$ molar. If desired, the upper limit can be reduced below $5 \times 10^{-4}$ molar, for example to less than 2.5 or $2 \times 10^{-4}$ molar, but with a similar lower limit giving a range, for example, of $10^{-4}$ molar to $10^{-5}$ molar. However, the effect on half life observed at $5 \times 10^{-4}$ molar is minimal and for practical purposes a range of $5 \times 10^{-4}$ molar to $10^{-4}$ molar will usually be suitable.

In terms of the amount of zinc in grams used to treat one litre of blood it will be appreciated that, as the controlling factor for optimisation of the treatment conditions is the concentration of zinc in the medium in which the red cells are treated, a conversion factor must take into consideration the difference in concentration of the red cells in the blood and in the medium. The reduction in volume from the former to the latter is usually of the order of one half so that, as a guide, it may be stated that a concentration of $10^{-4}$ molar usually corresponds approximately to the use of about 0.003 grams of zinc per litre of blood. Thus, although amounts of 0.2 to 0.4, for example 0.3, grams of zinc per litre of blood may be used, the desired aim of avoidance of a reduction of half life requires the use of lower amounts of about 0.03 to about 0.0003 grams of zinc per litre of blood, particularly about 0.015 to about 0.003 grams.

The present invention thus includes a process for the extracorporeal treatment of erythrocytes from a patient having sickle cell disease to effect binding of their haemoglobin with zinc which comprises contacting the erythrocytes with a neutral 2:1 ligand:zinc(II) complex containing two monobasic, bidentate ligands, at least one of which is provided by a compound being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms.

The processing of the blood outside the body in the process of the present invention may conveniently be carried out using either a closed sterile system specifically designed for the purpose or standard equipment which is available for the processing of blood in other contexts. In the latter case the system is an open one, the open parts of the procedure conveniently being carried out in a laminar flow cabinet of the type in which such manipulations of blood are generally carried out to maintain sterility. Blood may conveniently be taken from the patient by venipuncture into a double bag blood collection system and treated as follows. The plasma is initially separated from the red cells by centrifugation and squeezed into the second bag which remains connected, a sterile, isotonic zinc complex solution then being added to the red cells and allowed to react for the appropriate time before centrifugation. The resulting clear solution is squeezed out of the bag and discarded, and sterile, isotonic saline is mixed with the red cells. The cells are centrifuged again and the supernatant again discharged, the plasma finally being squeezed back and mixed with the red cells. The blood is then returned to the patient, The procedure will be repeated as already described above. It may be convenient, in order to ensure that no sickled cells are reinfused into the patient, to add a small amount of sterile oxygen to the blood at the end of the procedure to oxygenate the haemoglobin thereby preventing sickle polymer formation.

The zinc complex will usually be added to the cells in the form of a solution in a physiologically acceptable diluent, for example physiological saline Practical Immunology, Hudson and Hay (editors), Blackwell Scientific Publications, 1980, page 336. The use of an excess of the ligand forming compound or compounds in preventing dissociation of the 2:1 complexes under certain conditions has been fully discussed in UK Patent Application No. 8427485 and its equivalents. Although the extra-corporeal use of the complexes described herein, involving as it does essentially neutral conditions and relatively high concentrations, does not present as many problems from the point of view of dissociation of the complexes as does oral administration, it may nevertheless often be worthwhile employing the complex together with an excess of the free ligand-providing compound or compounds. A preferred range for the molar proportion of the free compound to zinc complex which is present when each ligand is identical is thus from 0 to 100 moles of free compound:1 mole of zinc complex. Conveniently, a proportion of up to no more than 50, 30 or especially 20 moles:1 mole is used with a lower level of 0.5, 1 or 2 moles:1 mole. A particularly preferred range is from 2 or 3 up to 18 or 20, or especially up to 30 or 50, moles of free compound: 1 mole of zinc complex, particularly 2 or 3, or especially 5, up to 8 or 10, especially up to 20, moles:1 mole. When there is more than one zinc bound ligand present in the composition, either in the form of a mixed ligand zinc complex and/or of a mixture of zinc complexes, then the proportion of each free ligand-providing compound to the zinc complex containing that ligand may conveniently also fall in the ranges indicated above. It will be appreciated, however, that when more than one ligandproviding compound is present it is less likely that the proportion of each will be towards the upper end of the broadest range of 0 to 100 moles of free compound:1 mole of zinc complex, the proportion being more likely to lie in a range of 0.5 to 50 moles:1 mole or such lower ranges as are quoted above. Indeed, the total molar concentration of both ligands (usually equimolar proportions) may often lie within the range indicated.

The use of the low concentrations of zinc complex which are suitable to avoid a reduction in the half life of the erythrocytes does preferably involve the use of an added amount of the free ligand or ligands to prevent undue dissociation of the complex at these low concentrations, the appropriate excess of free ligand increasing with a decrease in the concentration at which the zinc complex is used. Thus, in order to optimise zinc uptake by erythrocytes at a physiological pH of 7.4, preferred ranges for the ratio of moles of free compound or, where two different ligands are present, of both compounds in total (usually in equimolar proportions):1 mole of zinc (as the zinc complex) are as follows: from 2:1 to 5:1 for $10^{-3}$ molar zinc; from 5:1 to 10:1 for $5 \times 10$ molar zinc; from 15:1 to 25:1 for $10^{-4}$ molar zinc; and from 20:1 to 30:1 for $10^{-5}$ molar zinc.

Once treated, the haemoglobin molecules should retain the attached zinc atoms for their lifetime and it is therefore possible to envisage the use of the present invention in a prophylactic treatment carried out, for example, every month, in order to maintain an adequate proportion of such molecules in the body. However, the more common use will be in the treatment of recurring sickle cell disease crises as these occur.

The present invention thus further includes a method for the treatment of a patient suffering from sickle cell disease which comprises treating the blood of the patient extra-corporeally with an amount effective in achieving binding of zinc to the haemoglobin of a neutral 2:1 ligand:zinc(II) complex in which at least one ligand is provided by a compound being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms.

A very important advantage of the zinc complexes described herein lies in the nature of the modification of the haemoglobin which they effect. Thus, the complexes do not change the Hill coefficient of the haemoglobin and hence, although the complexes cause a left-shift of the oxy-haemoglobin dissociation curve, they do not prevent the haemoglobin functioning to donate oxygen to the tissues even though this may occur at a somewhat reduced level. This is an important property since any drug which prevents the haemoglobin functioning does of course have disadvantages, particularly for use in a patient in whom the haemoglobin level is lower than normal, as will be the case with patients suffering from sickle cell disease.

As an alternative to the extra-corporeal treatment of the blood of a patient with sickle cell disease the complexes can be administered directly to the patient, a possibility which is available owing to the unexpectedly low concentrations of the complex which have been found to effect an enhancement of the oxygen binding ability of the patient's haemoglobin. In this case the zinc complexes may be administered in the form of compositions, which may preferably contain amounts of the free ligand(s), as described in U.K. Patent Application No. 8427485 and its equivalents, administration by injection being of particular interest although oral administration may also be considered. By way of guidance upon dosage levels it may be stated that, for administration by injection to the average adult with an 8 liter blood volume, a treatment involving a dosage of zinc (in the form of the complex) in the range of 10 to 50 mg, for example 25 mg, will often be suitable (adjusted pro rata for the smaller blood volume in the case of children), oral dosage levels being similar or somewhat higher, for example up to 100 mg. The complex is usually administered in the presence of an amount of the free ligand(s), for example using 5 to 10 moles of the free compound(s):1 mole of zinc in the case of a 25 mg dose with a decrease in the amount of the free compound(s) for a higher dose and an increase for a lower dose, for example in a range from 2 or 3 up to 18 or 20, or especially up to 30 or 50 moles of free compound(s):1 mole of zinc complex, particularly 2 or 3, or especially 5, up to 8 or 10, especially up to 20, moles:1 mole. Such a systemic treatment may if necessary be repeated on several successive days, particularly when using doses at the lower end of the range indicated, and can be used either in the treatment of sickle cell crises or prophylactically, for example at monthly intervals.

It should be appreciated that the zinc complexes described above are of use in any other situation, in addition to sickle cell disease, where such a modification of the haemoglobin with the consequent enhancement of its ability to take up oxygen is advantageous. Thus, the invention is also of interest in the treatment of medical conditions involving pulmonary dysfunction such as emphysema, which involves a deterioration of the lung membranes, and also chronic bronchitis. The mode of treatment of the patient's blood in these other situations will be similar to that described for use in the treatment of sickle cell disease, being either a systemic or particularly an extra-corporeal treatment.

The present invention thus further includes a neutral 2:1 ligand:zinc(II) complex in which at least one ligand is provided by a compound being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms for use in the manufacture of a medicament for use in enhancing the oxygen binding affinity of haemoglobin, such a medicament being applicable in any context in which such an enhancement is beneficial.

Figure 1A:
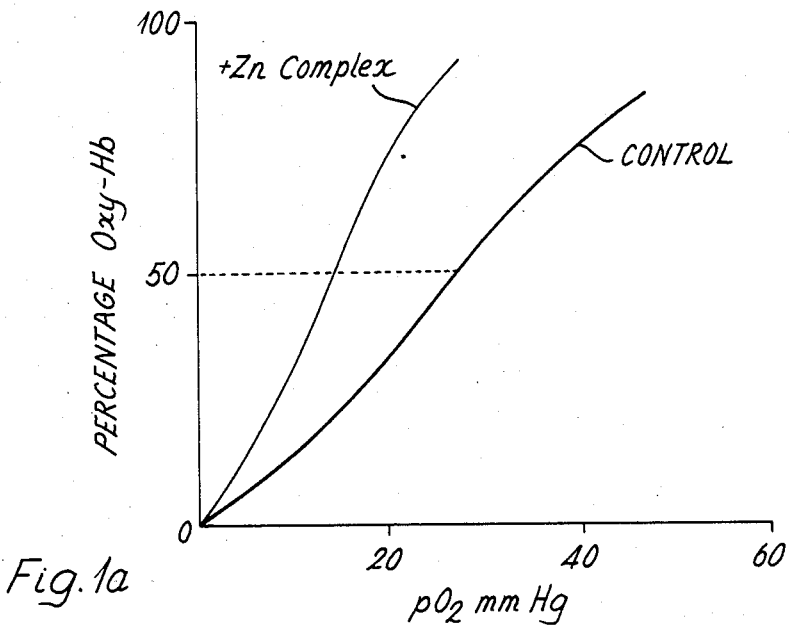
FIGS. 1a, 1b, 2 and 3 graphically show results obtained using Zn complexes as claimed herein compared to a control.

The invention is illustrated by the following Examples.

EXAMPLE 1

Uptake of zinc from complexes by haemoglobin (1) A 5% suspension of human erythrocytes in aqueous sodium chloride (130 mM) buffered to pH 7.4 by 20 mM Tris hydrochloride (2 ml) was incubated for 1 hour at 37° C. with the 2:1 zinc(II) complex in the presence of an excess of the ligand-forming compound. The complex was formed in situ in the buffer using $^{65}$Zn labelled ZnSO$_4$ at a concentration selected over a range from $1\times10^{-6}$ to $4\times10^{-3}$ M compound at ten times this concentration and a small amount of Tris free base (to about 2 mM) added to the medium to avoid an acid pH on reaction of the ZnSO$_4$ and the compound to form the complex. Following the period of incubation, an aliquot of the erythrocyte/medium mixture was placed above a layer of silicone oil and the erythrocytes separated by -30 centrifugation through the oil. The $^{65}$Zn levels associated with the erythrocytes and the incubation medium were then counted and the distribution ratio (concentration in erythrocytes/concentration in medium) calculated. The average distribution ratios of zinc obtained in a series of experiments for the homogeneous 2:1 complex from the ligand-providing compounds 3-hydroxy-2methyl-4-pyrone, 2-ethyl-3-hydroxy-4-pyrone and 3-hydroxy-2-(1'-methylethyl)-4-pyrone at a concentration of $5\times10^{-4}$M are shown in Table 1 together with the percentage of the total amount of zinc which is absorbed in the erythrocytes.

TABLE 1

| | Uptake of zinc by haemoglobin | |
|---|---|---|
| Ligand-providing compound | Distribution ratio | Percentage of zinc absorbed |
| 3-hydroxy-2-methyl-4-pyrone | 8 | 54 |
| 2-ethyl-3-hydroxy-4-pyrone | 300 | 96 |
| 3-hydroxy-2-(1'-methylethyl)-4-pyrone | 550 | 98 |

There was no evidence of any saturation of the rate of uptake over the concentration range studied so that the complex is not actively transported and, in order to account for the high distribution ratios observed, the zinc must therefore dissociate from the complex and bind to a macromolecule or membrane associated with the erythrocyte. The experiment just described was repeated at a concentration of 2.5 mM $^{65}$ZnSO$_4$ and 25 mM 2-ethyl-3-hydroxy-4-pyrone using erythrocyte ghosts in which the haemoglobin is lacking rather than whole erythrocytes. Only a low level of uptake of zinc was observed indicating that membrane binding is not responsible for the high distribution ratios observed with the whole erythrocytes. (2) The ability of the zinc-(II) complex of 2-ethyl-3-hydroxy-4-pyrone to donate zinc to haemoglobin was investigated by studying the elution profile of the $^{65}$Zn label when a mixture of haemoglobin and the $^{65}$Zn-labelled complex (at 1 mM concentration) in NaCl (130 mM) buffered to pH 7.4 by Tris hydrochloride is applied to a PD-10 colum (Sephadex G-10 gel permeation column—Pharmacia). It was found that, even when the free 2-ethyl-3-hydroxy-4-pyrone is present in an amount providing a 20-fold molar proportion of the ligand-providing compound-:zinc, the zinc is found to bind tightly to haemoglobin.

It is clear from this experiment that zinc binds more tightly to haemoglobin than to 2-ethyl-3-hydroxy-4-pyrone and this binding property, coupled with the high concentration of haemoglobin in erythrocytes, amounting to about 33% by weight, accounts for the very high distribution ratios obtained in (1).

EXAMPLE 2

Effect of the zinc complex of 2-ethyl-3-hydroxy-4-pyrone on the oxygen affinity of haemoglobin (1) A 50% suspension of human erythrocytes in pH 7.09 8BisTris/NaCl buffer 0.05M BisTris(bis(2-hydroxyethyl)imino-tris(hydroxymethyl)methane and 0.13M NaCl was incubated for 15 minutes at 37° C. with the 2:1 zinc(II) complex of 2-ethyl-3-hydroxy-4-pyrone in the presence of an excess of the ligand-forming compound, the complex being formed in situ using zinc sulphate and a 10 molar excess of 2-ethyl-3-hydroxy-4-pyrone (to provide the 2:1 complex and an 8 molar excess of the pyrone). The oxygen dissociation curve of the erythrocytes was then determined using the method of Bellingham and Huehns (Nature, 1968 218, 924–926) which involves measuring the change of OD at two wavelengths (570 and 555 nm) after the sequential measured addition of oxygen in a tanometer. The experiment was conducted using normal erythrocytes, 2,3-diphosphoglyceric acid (DPG) depleted erythrocytes, foetal erythocytes and sickle erythrocytes. A 2.5 mM concentration of zinc was employed in each case together with a proportion of erythrocytes such as to provide a 2:1 ratio of zinc:haemoglobin and consequent saturation of the haemoglobin by zinc, except in one experiment where the proportion was varied to provide a ratio varying from 0.5:1 to 2:1. In each case a control was carried out in the absence of any zinc sulphate or 2-ethyl-3-hydroxy-4-pyrone and in one case two additional controls were carried out in the presence of one of these compounds used alone. The values for p($O_2$)50 (i.e. the oxygen pressure at which 50% of the haemoglobin is in the oxygenated form) obtained in each case are shown in Table 2 (together with the inferred Zn:Hb ratio) from which it will be seen that the oxygen affinity of normal erythrocytes, and also of sickle erythrocytes, is increased through treatment of the cells with zinc(II) (2-ethyl-3-hydroxy-4-pyrone)$_2$. Foetal erythrocytes, which contain Hb-F and therefore show different characteristics from normal eythrocytes which contain Hb-A, were as expected not affected. The results show that with normal haemoglobin the zinc complex is producing a left-shift of the oxy-haemoglobin dissociation curve, i.e. the equilibrium in the reaction $HbO_2 = Hb + O_2$ has been displaced in favour of the $HbO_2$. With sickle erythrocytes the effect is even more marked as is further illustrated in (2) below.

(2) The effect of the 2:1 2-ethyl-3-hydroxy-4-pyrone:-zinc(II) complex on normal and sickle erythrocytes was further compared using a basically similar procedure to that described in 1) above. Concentrations of 2.5 mM $ZnSO_4$ and 25 mM pyrone, and a 2:1 Zn:Hb ratio were again used but the incubation period was extended to 1 hour. In each case a control experiment was carried out in the absence of any zinc sulphate or pyrone.

Figure 1B:
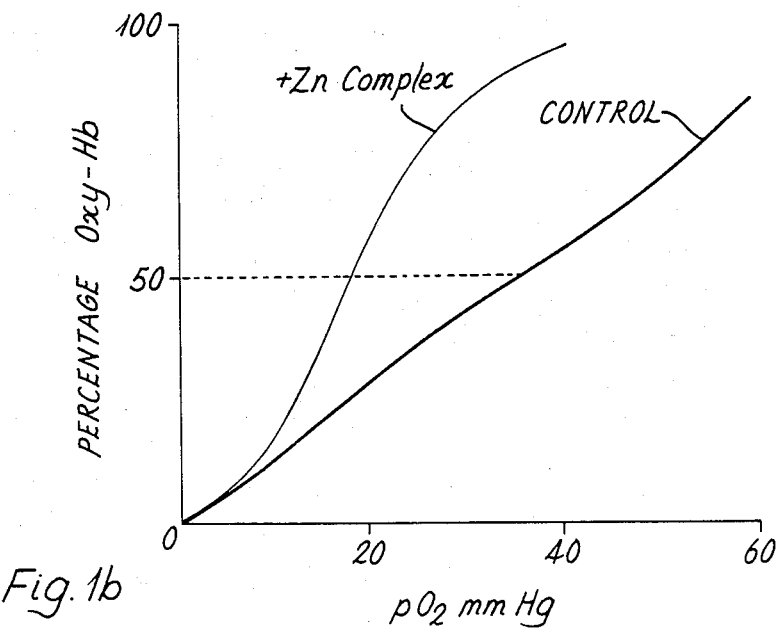

The results obtained are shown in FIG. 1, where (a) relates to the normal erythrocytes and (b) to the sickle erythrocytes, from which it will be seen that a significant left shift in the oxygen dissociation curve is produced in both cases but that the difference from the control is more marked for the sickle erythrocytes which are right shifted relative to the normal erythrocytes prior to treatment. Thus, the p($O_2$)50 values are control=27.5 mm Hg, treated cells=15.0 mm Hg (shift 12.5 mm Hg) for the normal

TABLE 2

| Cells | Oxygen affinity haemoglobin | | |
|---|---|---|---|
| | Addition to medium | Zn:Hb ratio | P($O_2$)50 mmHg |
| Normal erythrocytes | None | 0:1 | 27.5 |
| " | 2.5 mM $ZnSO_4$ + 25 mM pyrone | 2:1 | 15 |
| Normal erythrocytes | None | 0:1 | 26 |
| " | 2.5 mM $ZnSO_4$ | 2:1 | 24.5 |
| " | 2.5 mM pyrone | 0:1 | 28 |
| " | 2.5 mM $ZnSO_4$ + 25 mM pyrone | 2:1 | 15.5 |
| DPG depleted erythrocytes | None | 0:1 | 15.75 |
| " | 2.5 mM $ZnSO_4$ + 25 mM pyrone | 2:1 | 9.25 |
| Normal erythrocytes | None | 0:1 | 30.0 |
| " | 2.5 mM $ZnSO_4$ + 25 mM pyrone | 0.5:1 | 23.5 |
| " | " | 1:1 | 17.0 |
| " | " | 1.5:1 | 15.0 |
| " | " | 2:1 | 15.0 |
| Foetal erythrocytes | None | 0:1 | 22 |
| " | 2.5 mM $ZnSO_4$ + 25 mM pyrone | 0:1[(1)] | 24 |
| Sickle erythrocytes | None | 0:1 | 36 |
| " | 2.5 mM $ZnSO_4$ + 25 mM pyrone | 2:1 | 18.5 |

[(1)]assumed no uptake by Hb-F.

erythrocytes and control=36.0 mm Hg, treated cells=18.5 mm Hg (shift 17.5 mm Hg) for the sickle erythrocytes.

Figure 2:
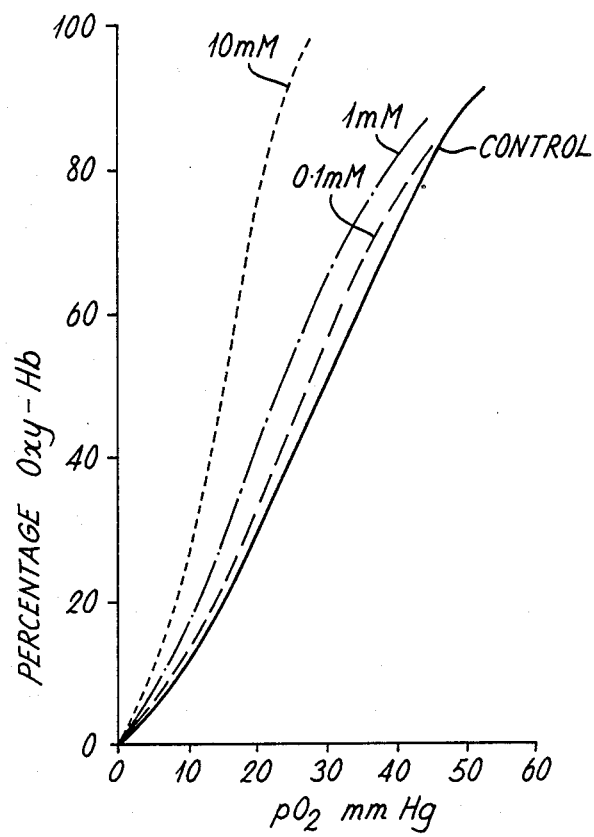

(3) The effect of different concentrations of the 2:1 2-ethyl-3-hydroxy-4-pyrone:zinc(II) complex upon normal erythrocytes was studied using a basically similar procedure to that described in (1) above but with $ZnSO_4$ concentrations of 0.1, 1 and 10 mM (and ten times these concentrations of the pyrone) and extending the incubation period to 1 hour. A control experiment was carried out in the absence of any zinc sulphate or pyrone. The results obtained are shown in FIG. 2 from which it will be seen that although there is a dose response effect there is still a discernible left shift in the oxygen dissociation curve at a concentration of the complex of 0.1 mM.

EXAMPLE 3

Treatment of rabbit blood with zinc complex of 2-ethyl-3-hydroxy-4-pyrone

Blood (4 ml) was venesected from the marginal ear vein of an adult New Zealand White rabbit and collected to obtain a final concentration of preservative free heparin of 20 international units/ml. The blood was washed with physiological saline and centrifuged at 2000 g to provide 0.5 ml of packed red blood corpuscles. These were incubated at 37° C. with an equal volume of either 2:1 2-ethyl-3-hydroxy-4-pyrone:zinc(II) together with an excess of the pyrone (0.1 mM $ZnSO_4$+2 mM pyrone) in physiological saline at pH 7.5 or of physiological saline alone at pH 7.5. After 30 minutes the cells were washed four times with physiological saline and then incubated at 37° C. with 15 μCi of $^{51}Cr$ labelled $Na_2CrO_4$ in 0.5 ml physiological saline at pH 7.5–8.0. After 30 minutes incubation in this second medium the cells were washed three times with physiological saline and then resuspended in physiological saline to a final volume of 1 ml with 50% of final haematocite. This solution was then injected into the marginal ear vein of the rabbit from which 1 ml blood samples were venesected daily at 2 day intervals for determination of survival of the treated cells in vivo through measurement of the radioactivity of the $^{51}$Cr. erythrocytes and control=36.0 mm Hg, treated cells=18.5 mm Hg (shift 17.5 mm Hg) for the sickle erythrocytes.

Figure 3:
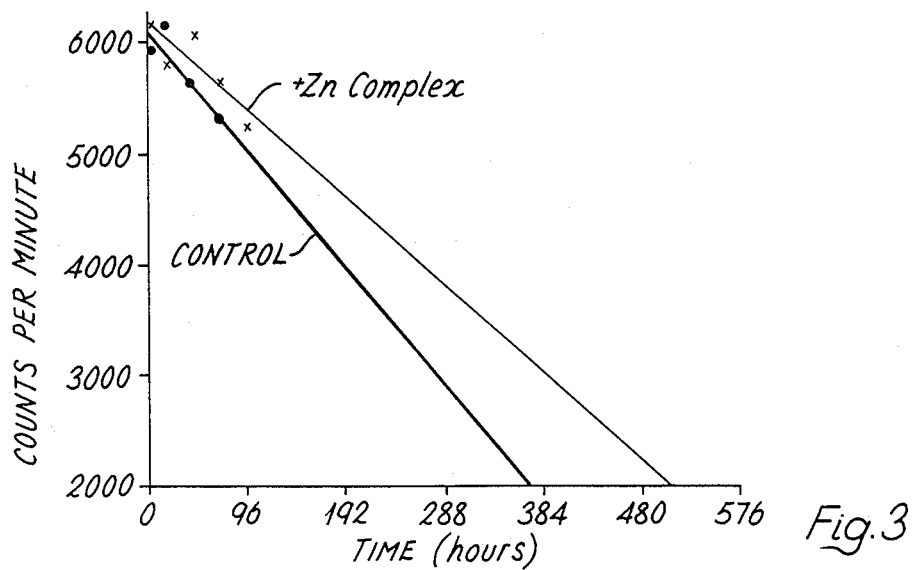

The results obtained are shown in FIG. 3 from which it will be seen that there is no indication of cell toxicity resulting from the treatment with the zinc complex. Indeed the treated red blood corpuscles show a slightly although not significantly longer survival rate than the untreated cells.

We claim:

1. A method for enhancing the oxygen binding affinity of halmoglobin in a patient in need of such treatment, said method comprising treating the blood of said patient with an amount effective to achieve such enhancement of a neutral 2:1ligand:zinc(II) complex in which at least one ligand is provided by a compound which is 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms.

2. A method according to claim 1, in which the patient is one suffering from sickle cell disease.

3. A method according to claim 1, in which the patient's blood is treated extra-corporeally.

4. A method according to claim 2, in which the patient's blood is treated extra-corporeally.

5. A method according to claim 3, in which the treatment of the blood is effected at a concentration of zinc in the form of the complex which is from $10^{-3}$ to $10^{-5}$ molar.

6. A method according to claim 5, in which the concentration is from $5 \times 10^{-4}$ to $10^{-4}$ molar.

7. A method according to claim 6, in which the complex is administered together with the uncomplexed compound or one or both of the uncomplexed compounds corresponding to the ligands, the molar ratio of the compound or both compounds in total to the zinc complex being from 5:1 to 25:1.

8. A method according to claim 1, in which each ligand of the complex is separately provided by a compound selected from the following compounds of types (1), (2) and (3):
   (1) 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms;
   (2) a 3-hydroxypyrid-2-one or 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, cycloalkoxy, aliphatic amide, aliphatic ester, halogen and hydroxy groups and, optionally, in which one or more of the hydrogen atoms attached to ring carbon atoms are replaced by one of said substituents, by an aliphatic hydrocarbon group of 1 to 6 carbon atoms, or by an aliphatic hydrocarbon group substituted by an alkoxy, cycloalkoxy, aliphatic ester, halogen or hydroxy group; and
   (3) an alternative compound providing a physiologically acceptable monobasic, bidentate ligand which is capable of bonding covalently to zinc; but with the proviso that at least one ligand is of type (1).

9. A method according to claim 8, in which the compound of type (3) either contains a first grouping which is an enolic hydroxy group or a carboxy group and a second grouping which is an amine group or a hydroxy group, or is a monocarboxylic acid providing an anion containing a grouping

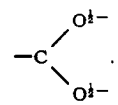

10. A method according to claim 8, in which each ligand separately is provided by a compound selected from those of type (1) and 3-hydroxypyrid-2-ones of type (2).

11. A method according to claim 10, in which the compound of type (2) is a 3-hydroxypyrid-2-one in which the hydrogen atom attached to the nitrogen atom is replaced by an aliphatic hydrocarbon group of 1 to 6 carbon atoms and, optionally, in which one or more of the hydrogen atoms attached to ring carbon atoms are replaced by the same or a different aliphatic hydrocarbon group of 1 to 6 carbon atoms.

12. A method according to claim 1, in which said complex is a neutral 2:1 3-hydroxy-4-pyrone:zinc (ii) complex in which each ligand is separately provided by a compound being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms.

13. A method according to claim 2, in which said complex is a neutral 2:1 3-hydroxy-4-pyrone:zinc(II) complex in which each ligand is separately provided by a compound being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms.

14. A method according to claim 1, in which the 3-hydroxy-4-pyrone ligand-providing compound is 3-hydroxy-4-pyrone or a 3-hydroxy-4-pyrone in which one or more of the hydrogen atoms attached to ring carbon atoms are replaced by an acyclic group of 1 to 4 carbon atoms.

15. A method according to claim 14, in which the compound is 3-hydroxy-4-pyrone or a 3-hydroxy-4-pyrone in which one or more of the hydrogen atoms attached to ring carbon atoms are replaced by the same or different substituents selected from methyl, ethyl, n-propyl, isopropyl and butyl groups.

16. A method according to claim 15, in which the substituted 3-hydroxy-4-pyrone has a single substituent at the 2- or 6-position.

17. A method according to claim 13, in which each ligand is separately provided by 3-hydroxy-2-methyl-4-pyrone, 2-ethyl-,3-hydroxy-4-pyrone, 3-hydroxy-2-(1-methylethyl)-4-pyrone or 3-hydroxy-2-propyl-4-pyrone.

18. A method according to claim 17, in which both ligands are provided by the same compound.

19. A method according to claim 1, in which the complex is the neutral 2:1 2-ethyl-3-hydroxy-4-pyrone: zinc(II) complex.

20. A method according to claim 1, in which the complex is the neutral 2:1 2-methyl-3-hydroxy-4-pyrone: zinc(II) complex.

21. A method according to claim 2, in which the complex is the neutral 2:1 2-ethyl-3-hydroxy-4-pyrone: zinc(II) complex.

22. A method according to claim 2, in which the complex is the neutral 2:1 2-methyl-3-hydroxy-4-pyrone: zinc(II) complex.

* * * * *